United States Patent
Jensen et al.

(10) Patent No.: US 10,880,289 B2
(45) Date of Patent: Dec. 29, 2020

(54) MEDICAL ENVIRONMENT SINGLE SIGN-ON SYSTEM

(71) Applicant: Welch Allyn, Inc., Skaneateles Falls, NY (US)

(72) Inventors: Eric P. Jensen, Niskayuna, NY (US); Michael D. Hoch, North Syracuse, NY (US); Stacie L. Brough, Syracuse, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 218 days.

(21) Appl. No.: 15/463,622

(22) Filed: Mar. 20, 2017

(65) Prior Publication Data

US 2018/0270220 A1    Sep. 20, 2018

(51) Int. Cl.
*H04L 29/06* (2006.01)
*G16H 10/60* (2018.01)
*H04L 29/08* (2006.01)
*G16H 40/67* (2018.01)

(52) U.S. Cl.
CPC ......... *H04L 63/0815* (2013.01); *G16H 10/60* (2018.01); *G16H 40/67* (2018.01); *H04L 67/12* (2013.01)

(58) Field of Classification Search
CPC ............. H04L 63/0815; H04L 63/0823; G06F 19/322; G06F 19/3418
See application file for complete search history.

(56) References Cited

U.S. PATENT DOCUMENTS

| | | |
|---|---|---|
| 2002/0120310 A1 | 8/2002 | Linden et al. |
| 2005/0201345 A1 | 9/2005 | Williamson |
| 2006/0219776 A1 | 10/2006 | Finn |
| 2009/0058598 A1 | 3/2009 | Sanchez Sanchez |
| 2009/0140043 A1* | 6/2009 | Graves ............... G06Q 10/087 235/380 |
| 2010/0154046 A1 | 6/2010 | Liu et al. |
| 2010/0235782 A1 | 9/2010 | Moore |
| 2011/0227856 A1* | 9/2011 | Corroy ............... H04B 13/005 345/173 |
| 2012/0011237 A1* | 1/2012 | Bagwandeen ......... G16H 40/63 709/223 |
| 2012/0023556 A1* | 1/2012 | Schultz ................. G06F 21/41 726/4 |
| 2012/0093294 A1 | 4/2012 | Lalena et al. |
| 2012/0293597 A1 | 11/2012 | Shipon |
| 2013/0132109 A1 | 5/2013 | Lakshminarasimhan |

(Continued)

OTHER PUBLICATIONS

Imprivata, Imprivata Confirm ID for Medical Devices, Feb. 2016, 2pgs.

(Continued)

*Primary Examiner* — Harunur Rashid
(74) *Attorney, Agent, or Firm* — Merchant & Gould P.C.

(57) ABSTRACT

A medical facility environment includes medical devices, single-sign on system devices, and an identity access management system (IAMS). A clinician logs into an electronic medical record system and/or facility workstation, typically at the start of a shift. Successful login opens a valid user session with the IAMS. Thereafter, clinicians having valid user sessions can record, save, and/or transmit patient vital signs by providing, only, a clinician identifier associated with the valid user session.

20 Claims, 5 Drawing Sheets

(56) References Cited

U.S. PATENT DOCUMENTS

| | | |
|---|---|---|
| 2013/0317852 A1 | 11/2013 | Worrell et al. |
| 2014/0330575 A1 | 11/2014 | Traughber et al. |
| 2015/0178447 A1 | 6/2015 | Cohen et al. |
| 2016/0004836 A1 | 1/2016 | Rybkin |
| 2016/0092665 A1 | 3/2016 | Cowan et al. |
| 2017/0011192 A1 | 1/2017 | Arshad et al. |
| 2017/0347993 A1* | 12/2017 | Anand .................. A61B 8/585 |

OTHER PUBLICATIONS

Cardiocomm Solutions, Inc., GlobalCardioTM EMR Integration, Aug. 5, 2016, 1pg.

International Search Report for corresponding International Patent Application No. PCT/US2018/019701, dated Jun. 4, 2018.

* cited by examiner

MEDICAL ENVIRONMENT SINGLE SIGN-ON SYSTEM

INTRODUCTION

During a typical shift, clinicians often visit multiple patients and interact with multiple computing devices, such as vital signs devices. These vital signs devices are password protected in many medical facilities and require clinicians to log in using an identifier and a second factor. In some instances, the medical facilities require the second factor to be a complex password.

Oftentimes, clinicians find such data entry of an identifier and a second factor to be cumbersome to the workflow and prone to user error. For example, a clinician wearing protective gloves may have trouble interacting with on-screen keyboards. Vital signs devices can be configured to lock out the user based on a number of failed attempts to log in properly. If a clinician is locked out of a vital signs device, intervention of information technology administrators can be necessary before proceeding with patient vital sign measurements.

SUMMARY

Embodiments of the disclosure are directed to a single sign-on system in a medical facility. In one aspect, a single sign-on system device includes a processing unit and system memory. The system memory includes instructions that, when executed by the processing unit, cause the single sign-on system device to: receive a clinician identifier via a first application program interface (API), where the clinician identifier is received from a medical device; determine whether the clinician identifier corresponds to an entry in a user database; transmit an authentication request to an identity access management system via a second API, where the request for authentication includes the clinician identifier; receive a confirmation, via the second API, that a clinician associated with the clinician identifier is associated with an open session and within a grace period; and transmit the confirmation to a vital signs device via the first API.

In another aspect, a medical device in a single sign-on system includes a processing unit and system memory. The system memory includes instructions that, when executed by the processing unit, cause the single sign-on system device to: receive a clinician identifier from a clinician; transmit the clinician identifier to a host; receive, from the host, an authentication result, the authentication result including successful authentication or unsuccessful authentication; if the authentication result is successful authentication, enable clinician login without requiring a second factor; acquire physiological data of a patient; store the physiological data; generate tagged physiological data including a clinician identifier field; and transmit the tagged physiological data to a central monitoring station.

In another aspect, a computer-implemented method in a single-sign on system includes: receiving a clinician identifier that uniquely identifies a clinician from a vital signs device; determining whether the clinician identifier corresponds to an entry in a user database; when the clinician identifier does not correspond to an entry in the user database, determining an alias identifier, the alias identifier being an identifier associated with a clinician in the user database; transmitting a request for authentication to an identity access management system, the request for authentication including the clinician identifier or the alias identifier; receiving a confirmation that a clinician associated with the clinician identifier or the known identifier is associated with an open session and within a grace period; and transmitting the confirmation to the vital signs device.

The details of one or more embodiments are set forth in the accompanying drawings and the description below. Other features, objects, and advantages of these embodiments will be apparent from the description, drawings, and claims.

DESCRIPTION OF THE DRAWINGS

The following drawing figures, which form a part of this application, are illustrative of described technology and are not meant to limit the scope of the disclosure in any manner.

DETAILED DESCRIPTION

Various embodiments of the present disclosure will be described in detail with reference to the drawings, wherein like reference numerals represent like parts and assemblies throughout the several views. Additionally, any examples set forth in this specification are not intended to be limiting and merely set forth some of many possible embodiments.

Broadly, the present disclosure is directed to improving clinician workflows in a patient care environment. Typical patient care environments include hospitals, urgent care centers, medical clinics, nursing homes, etc. During a typical work shift, clinicians move about the patient care environment and interact with a plurality of computing devices. Because of the nature of the data inputted and accessed by the computing devices, most patient care environments have security measures on the computing devices. In such patient care environments, clinicians can only access and/or associate patient data with a patient's electronic record after the clinician has been authenticated.

Patient care environment systems manage security on computing devices in various ways. In some instances, the computing devices used within these patient care environments require clinician login and a second factor, such as a secure password. Other patient care environments use single sign-on systems where a monitoring device conducts and manages the entirety of the authentication process.

Figure 1:
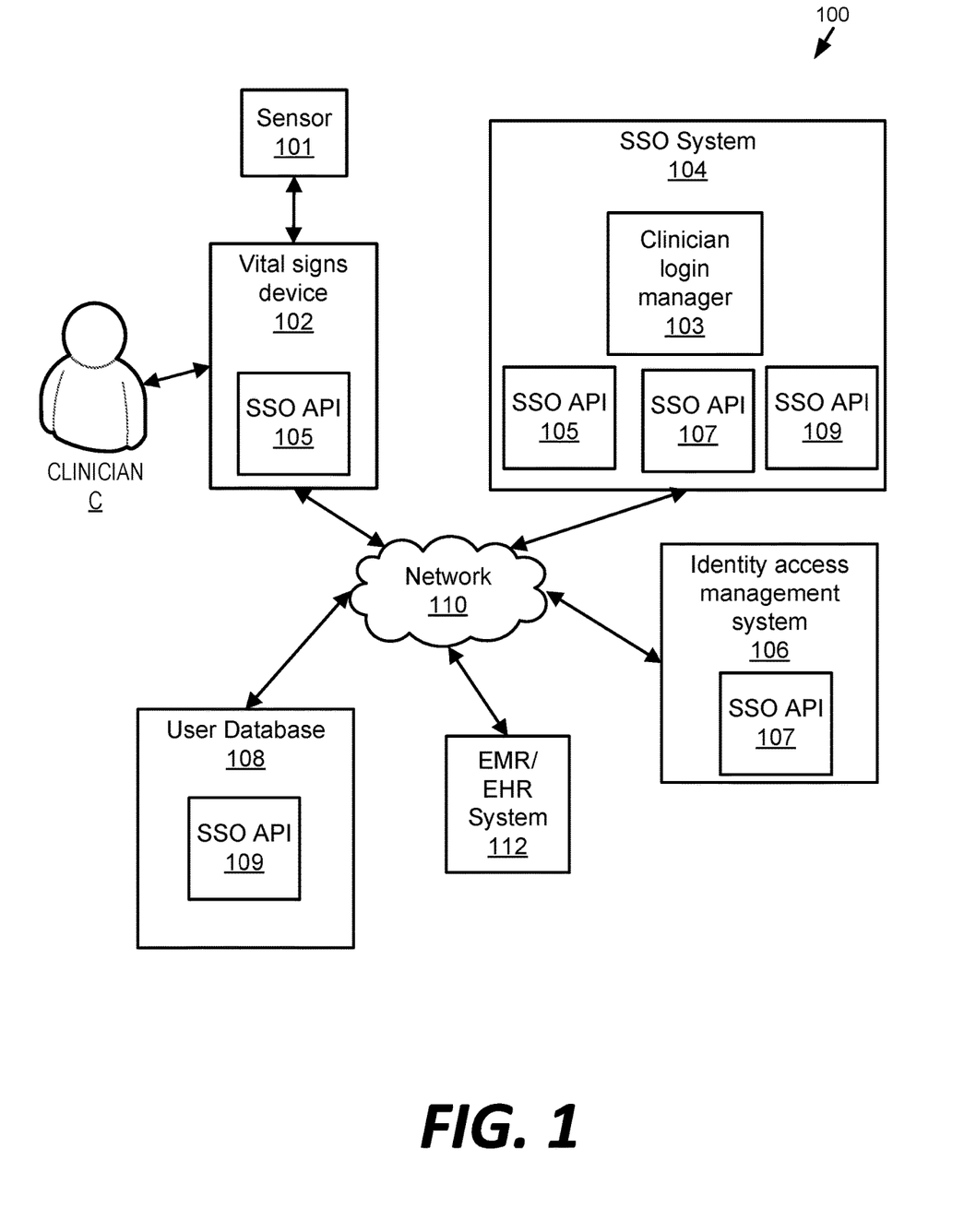
FIG. 1 is a schematic view of an example environment of a medical facility single sign-on system.

FIG. 1 is a schematic diagram of an example environment 100 of a medical facility single sign-on system. As used herein, the term "single sign-on (SSO) system" refers to a computing environment where a user is able to provide login credentials (typically, a user ID and password) and access multiple applications and/or devices within the computing environment. Environment 100 includes sensor 101, vital signs device 102, single sign-on system 104, identity access management system 106, user database 108, and electronic medical record/electronic health record system 112. Each component 102, 104, 106, 108, and 112 is in communication with network 110. Clinician C interacts with vital signs device 102. Other embodiments can include more or fewer components and/or users.

Vital signs device 102 provides an interface for the clinician C to interact with the patient's electronic records and/or one or more various vital sign measuring components, such as sensor 101. Example vital signs device 102 include the Connex® Spot Monitor and the Connex® Vital Signs Monitor, both manufactured by Welch Allyn, Inc. of Skaneateles Falls, N.Y.

Vital signs device 102 includes SSO application programming interface 105 that enables the vital signs device 102 to communicate with the SSO system 104. Generally, clinician C interacts with vital signs device 102 in the present disclosure by first providing a clinician identifier. The clinician C can provide a clinician identifier in a variety of ways, such as by scanning a barcode, typing a user name, and using a NFC or RFID-enabled badge. Clinician C is a health care provider, such as a nurse, nurse practitioner, physician's assistant, physician, and the like. Additionally, clinician C is associated with the medical facility.

After clinician enters his or her clinician identifier, the clinician waits for confirmation of that clinician identifier within the single sign-on system. Upon authentication confirmation, clinician C can proceed to record one or more vital signs of a patient. Vital signs device 102 includes one or more of the computing components shown below and is described with reference to FIG. 5.

Vital signs device 102 is configured to receive physiological data (termed "vital signs data" herein) of a patient from sensor 101. Sensor 101 includes one or more components capable of acquiring physiological data. Examples of sensor 101 include a temperature, heart rate, respiration rate, and $SpO_2$ sensors, and the like. Other types of sensors are contemplated.

Notably, vital signs device 102 does not host a thin client application to manage single sign-on workflows. Rather, the aspects and functionality of the instantly disclosed systems and methods eliminate the need for such a thin client application.

SSO system 104 communicates between various components within environment 100 and facilitates clinician login. Communication and clinician login management is provided by clinician login manager 103, which is hosted by SSO system 104. Example computing components of SSO system 104 are shown and described with reference to FIG. 5, below.

SSO system 104 can receive and obtain data to/from other system 100 components via one or more application programming interfaces (APIs). As shown, SSO system 104 includes SSO API 105 for communication with vital signs device 102; SSO API 107 for communication with IAMS 106; and SSO API 109 for communication with user database 108.

Example communications include receiving a clinician identifier from vital signs device 104 and determining whether that identifier corresponds to an identifier known by or accessible by IAMS 106. SSO system 104 can be configured to receive access to user database 108 to conduct lookup procedures in user database 108 before transmitting the identifier to IAMS 106. In some instances, SSO system 104 determines whether the clinician identifier corresponds to an entry in user database 108 and correlates the clinician identifier with an aliased ID.

SSO system 104 can also provide security certificates to IAMS 106 as part of, or before, requesting authentication of a clinician identifier. SSO system 104 receives responses from IAMS 106 and transmits those responses to vital signs device 102.

In some implementations, SSO system 104 is multiple components and/or devices: a host and a single sign-on software service. The host can serve as an interface between a client network and vital signs device 102. The single sign-on software service performs the more complex processing tasks for the host.

Identity access management system (JAMS) 106 manages clinician badge authentication for the patent care facility. In some instances, IAMS 106 can be implemented as a web service. Typically, IAMS 106 maintains a database of clinicians having open authentication sessions. After a clinician logs in, usually at the beginning of a shift, IAMS 106 manages the duration of time that clinician's session remains valid (or within a grace period). The time can be a set period of time after login and/or related to the start or end times of the clinician's scheduled shift.

IAMS 106 is a distinct system from SSO system 104 and is in communication with network 110. IAMS 106 can include SSO API 107 enabling communication with SSO system 104, such as calls, requests, etc., regardless of differences in software platforms. In this way, system 100 can be agnostic to the particular IAMS provider.

IAMS 106 receives identifier information from SSO system 104. In some instances, IAMS 106 also receives a request for authentication with the identifier information. Upon receiving the identifier information, IAMS 106 locates that identifier and determines whether that identifier corresponds to an identifier that is within an open authentication session. In some implementations, users in IAMS 106 are provided with a grace period token that expires at a given time or after a predetermined amount of time.

If the identifier does not correspond to an entry in IAMS 106, IAMS 106 can also determine whether an alias ID, such as an EMR number or user name, employee number, etc., has an open authentication session. This determination can include communicating with, or searching within, user database 108.

User database 108 is a database of users in the patient care environment 100. Examples of user database 108 include an Active Directory and Lightweight Directory Access Protocol (LDAP). Each user entry in user database 108 can include more than one identifier associated with a clinician, such as an EMR user name, badge number, employee number, network ID number, email address, etc. Via SSO API 109, user database 108 supports identifier lookup using, for instance, one or more of the example identifiers named above.

System 112 is either an electronic medical record (EMR) system or an electronic health record (EHR) system. An example system 112 is the Acute Care Electronic Medical Record by Cerner™ of Kansas City, Mo. System 112 receives vital sign data and vital sign user/clinician data and archives or associates those data with the patient's chart as confirmed data.

One or more components of environment 100 are in communication with each other via network 110. Network 110 may include any type of wireless network, a wired network, or any communication network known in the art. For example, wireless connections can include cellular network connections and connections made using protocols such as 802.11a, 802.11g, 802.11n, and/or 802.11ac. In other examples, a wireless connection can be accomplished directly between the vital signs device 102 and an external display using one or more wired or wireless protocols, such as Bluetooth, Wi-Fi Direct, radio-frequency identification (RFID), or Zigbee. Other configurations are possible.

Figure 2:
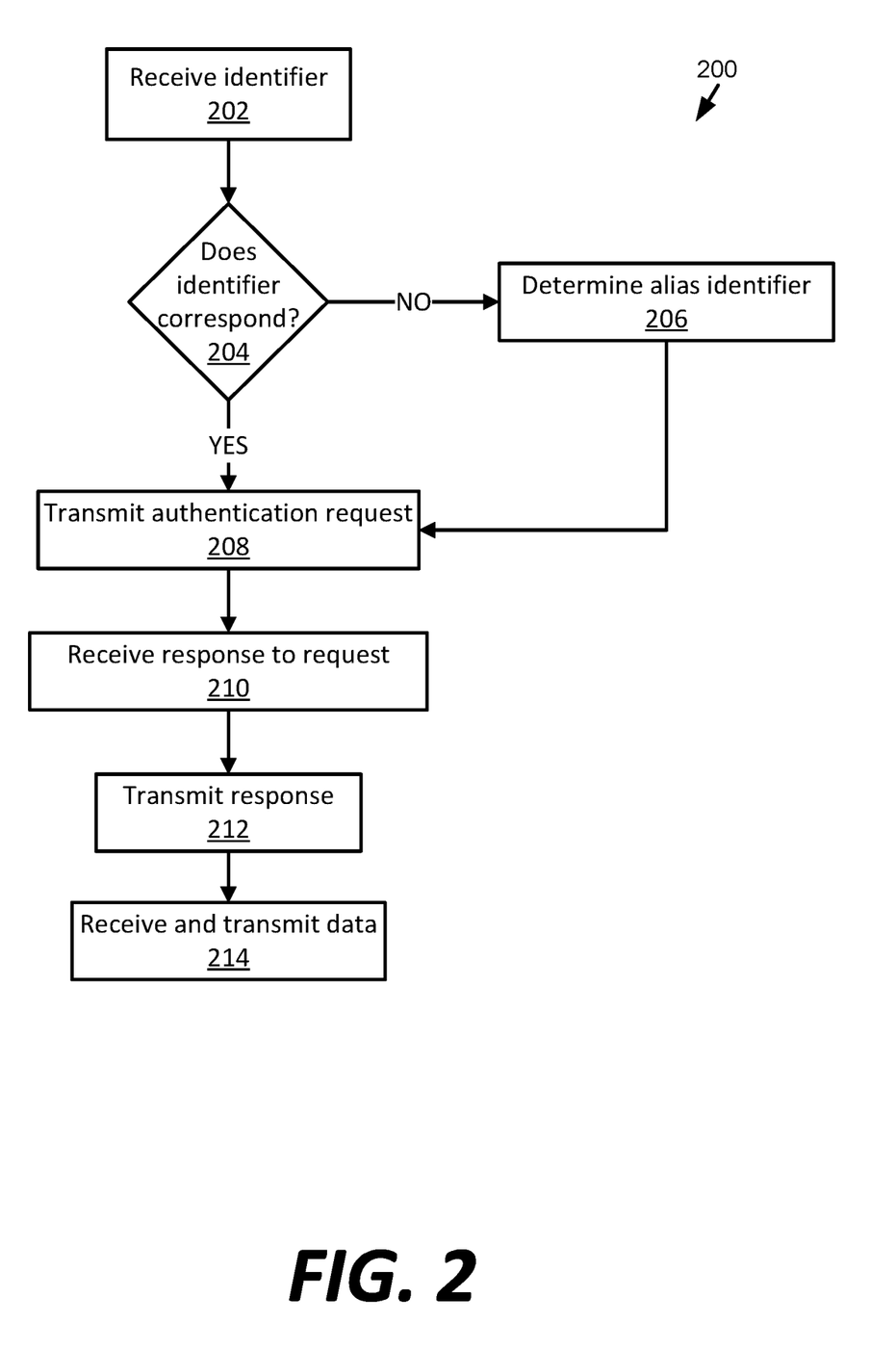
FIG. 2 illustrates an example method for authenticating a received clinician identifier.

FIG. 2 shows an example flowchart of a method 200 for authenticating a clinician identifier. The example method includes receiving an identifier (operation 202), determining whether the identifier corresponds to an entry (operation 204), determining an alias identifier (operation 206), transmitting an authentication request (operation 208), receiving a response to a request (operation 210), transmitting a response (operation 212), and receiving and transmitting data (operation 214). Example method 200 is from the perspective of the single sign-on system 104 shown and described with reference to FIG. 1. Other embodiments can include more or fewer operations.

Method 200 begins by receiving an identifier (operation 202). The identifier is received via network 110 and typically is transmitted from vital signs device 102. The identifier is inputted by a clinician at the vital signs device 102 and can be the clinician's EMR user name, employee number, network ID number, or other identifier. The identifier may include the result of a bar code scan, RFID tag transmission, and/or a user name. Notably, a second factor, such as, a password, is not included and not received in operation 202.

An example messaging schema received during operation 202 is provided below:
[Header]
[Vital signs device ID]
[Clinician ID]
[Footer]

In the schema above, the Header portion includes typical Header data known in the art. Example Header content includes file length and content. The vital signs device ID portion includes an identifier of the vital signs device that sent the message. Additionally, the vital signs device ID portion can include a return address for the vital signs device. The Clinician ID portion includes the Clinician ID received by the vital signs device from the clinician. The Footer portion includes typical Footer data known in the art. Example Footer content includes an indication of the message's end and checksum characters.

Upon receiving the identifier (operation 202), a determination is made whether the identifier corresponds to an entry in a user database (operation 204). One example of a user database is shown in, and described with reference to, FIG. 1 above. Operation 204 can include cross-referencing an active directory and/or a lightweight directory access protocol. The directory or LDAP may be queried for a network ID, EMR-ID, employee number, etc. If the identifier corresponds to an entry then method 200 proceeds to operation 208. If the identifier does not correspond to a directory, then method 200 proceeds to determine an alias identifier (operation 206).

Determining an alias identifier (operation 206) includes locating a known identifier for the clinician and correlating that with the identifier received in (operation 202). Typically, operation 206 includes querying a user information database, such as the user information database 108 shown in FIG. 1, or some other active directory. In order to access the user information database, the single sign-on system device can provide a stored security certificate. This stored security certificate is provided to the identity access management system or the user database. Thereafter, the single sign-on system device receives access to the user database.

After receiving access to the user database, an alias identifier is determined (operation 206) by executing a look-up procedure on the user database. The user database can include one or more types of identifiers, such as a network ID, EMR-ID, a badge number, an employee number, etc., and one or more of these known identifiers is correlated to the identifier received in operation 202. In an alternative embodiment, method 200 involves transmitting a request to the user database or the identity access management system to determine an alias identifier.

In operation 208, an authentication request including either the identifier or the alias identifier is transmitted to the identity access management system. The identity access management system in turn references a database of user log-ins to determine whether the identifier corresponds to a user who has a valid session still open.

An example messaging schema for a transmission to the IAMS in operation 208 is provided below:
[Header]
[SSO system device ID]
[Clinician identifier or alias ID]
[Request to authenticate]
[Footer]

In the schema above, the Header portion includes typical Header data known in the art. Example Header content includes file length and content. The SSO system device ID portion includes an identifier of the SSO system device that sent the message. The SSO system device ID portion can additionally include a return address. The Clinician identifier or alias ID portion includes the Clinician ID received by the vital signs device from the clinician or the alias ID determined in operation 206. The request to authenticate portion includes instructions requesting the authentication of the clinician identifier or alias ID. The Footer portion includes typical Footer data known in the art. Example Footer content includes an indication of the message's end and checksum characters.

After transmitting the authentication request (operation 208), the single sign-on system device receives a response to that request (operation 210). Receiving the response (operation 210) can additionally include, in some instances, receiving a validation period and/or determining whether the user is within the validation period. A validation period is a period of time during which a user single sign-on is enabled within the patient care environment.

After receiving a response (operation 210), method 200 proceeds to transmit a response (operation 212). During operation 212, the single sign-on system device transmits the response to the vital signs device 102. The response includes authentication result, which can include either an indication of successful authentication or unsuccessful authentication. Additionally, the response can include the alias identifier. The vital signs device 102 can retain and use the alias identifier for subsequent data transmissions, such as operation 214. In effect, the authentication result is a confirmation or denial that a clinician associated with the clinician identifier is within an open session and within a grace period. A grace period is a pre-determined amount of time for either the employees within the patient care facility and/or the type of employee within the patient care facility, typically corresponding to a shift duration.

Method 200 can additionally include receiving and transmitting data (operation 214). The single sign-on system device can receive messages including vital sign data of a patient as well as vital signs device user data. In turn, those data are transmitted to an electronic medical record system and/or a record within an electronic medical record system corresponding to the patient being examined.

Figure 3:
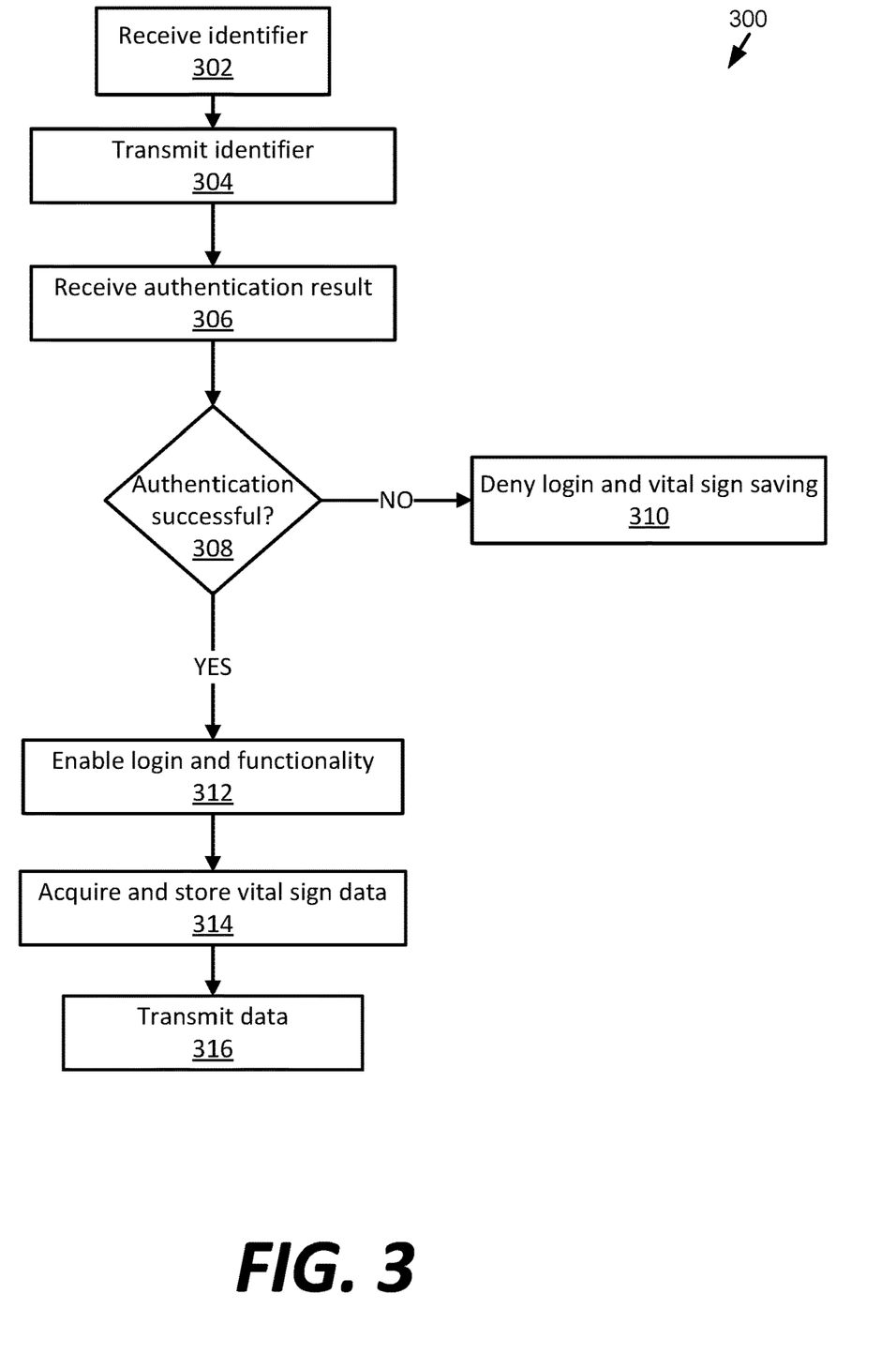
FIG. 3 illustrates an example method for managing a clinician login at a vital signs device.

FIG. 3 is an example flowchart of a method 300 for managing clinician login at a vital signs device. The example method 300 includes receiving an identifier 302, transmitting an identifier (operation 304), receiving an authentication result (operation 306), determining whether authentication was successful (operation 308), denying login (operation 310), enabling login and functionality (operation 312), acquiring and storing vital sign data (operation 314), and transmitting data (operation 316). As shown, vital signs device 102 performs the operations of example method 300. Other embodiments can include more or fewer operations.

Before operation 302, a clinician has previously logged into an open session at a work station. The method 300 begins by receiving an identifier (operation 302). Receiving an identifier (operation 302) includes displaying a clinician ID field on a display of the vital signs device, and enabling the clinician to enter a clinician ID into the clinician ID field. As discussed above, the identifier may be entered using any one of a keyboard, voice recognition, a bar code scan, and/or a communication enabled badge.

Upon receiving the identifier, the identifier is transmitted (operation 304) to an external service for validation. In the example shown, the external service is a single sign-on system 104. In some instances, the recipient is a host that is part of single sign-on system 104.

Then, an authentication result is received (operation 306) from the authenticating service. A determination of whether the authentication is successful (operation 308) includes analyzing the received communication to determine if there was successful authentication or unsuccessful authentication. If authentication was unsuccessful, the vital signs device can be configured to deny login and prevent the clinician from saving any vital sign data (operation 310). In some instances, the vital signs device may still allow the clinician to record or obtain vital sign data, but prevent saving those data in the patient's electronic medical record.

If the authentication result is a successful authentication, then login and functionality are enabled (operation 312). In some instances, the vital signs device can display a different user interface to the clinician than if the authentication result was unsuccessful, as in operation 310.

Then, the vital signs device can acquire and store vital sign data (operation 314). As mentioned above, vital signs device 102 can receive vital signs data from a variety of components configured to measure and/or obtain vital signs of the patient. Additionally, acquiring and storing vital signs data (operation 314) can include generating tagged physiological data. Tagged physiological data can include a clinician identifier field either as part of the data or as metadata of the file. Clinician identifier field can store the identifier received in operation 302, or one or more other types of identifiers, such as EMR ID, employee ID, and/or first or last name of the clinician.

Last, vital signs device can transmit vital sign data (operation 316) to the single sign-on system device and/or an electronic medical record.

Figure 4:
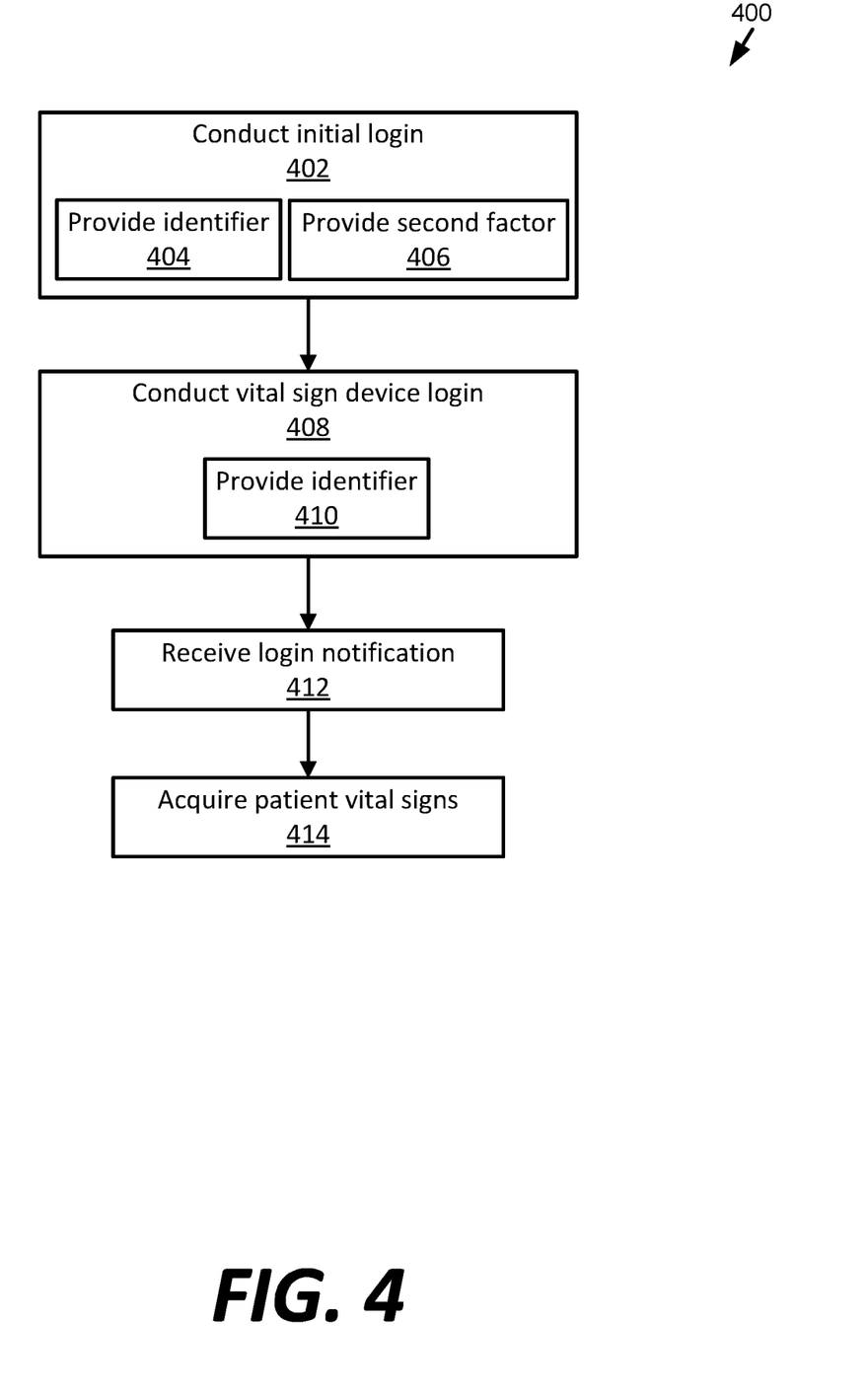
FIG. 4 illustrates an example method for using a vital signs device in a single sign-on environment.

FIG. 4 shows an example flowchart of a method 400 of using a vital signs device in a single sign-on environment. The example method 400 includes conducting initial login (operation 402), conducting a vital signs device login (operation 408), receiving a login notification (operation 412), and acquiring patient vital sign (operation 414). A clinician in a patient care environment, such as a nurse, doctor, nurse practitioner, and the like, typically conducts operation 400. Other embodiments can include more or fewer operations.

Example method 400 begins when the clinician conducts an initial login (operation 402). At some time during their work shift at the patient care facility, the clinician logs into a work station. In most cases, the clinician performs this initial login at the beginning of their shift, although the login may occur at any time during their shift. The work station is in communication with an identity access management system and a network. The clinician provides an identifier (operation 404) and provides a second factor (operation 406). Providing an identifier (operation 404) usually involves a user login, such as an EMR user name, an employee number, a network ID number or other identifying names. Then the clinician provides a second factor (operation 406), the second factor usually being a password. In some instances, alternative authentication means may be used for the second factor, such as presenting the clinician with a one-time pass code that they must enter into the work station.

After the clinician has conducted an initial login (operation 402), the clinician may conduct the vital signs device login (operation 408) at one or more various locations throughout the patient care environment. Logging in at the vital signs device (operation 408), differs from the initial login (operation 402), in that the clinician need only provide an identifier (operation 410). The clinician can provide the identifier to the vital signs device in a variety of ways. For example, a clinician can begin using an on-screen or physical keyboard by typing their user name, scan a bar code under a bar code reader, and/or use an NFC- or RFID-enabled badge to communicate with the vital signs device. In those various instances, the vital signs device includes necessary components to receive the types of identifying information, such as a bar code reader, NFC transceiver, and RFID transceiver.

After providing the identifier to the vital signs device (operation 408), the clinician receives a login notification (operation 412). The login notification is an authentication result including an indication of either successful authentication or unsuccessful authentication. If the authentication result is successful authentication, the vital signs device enables the clinician login without requiring a second factor. In other words, if the authentication is successful, the clinician may proceed to record the vital signs and/or access electronic medical records relating to the patient without requiring additional action on the part of the clinician.

In most instances, the vital signs device is configured to require a clinician ID to save any measurements received by the vital signs device. Accordingly, if the authentication result is successful, the clinician may proceed to acquire patient vital signs (operation 414). At this point, the clinician may use one or more peripheral sensor devices to obtain/record patient vital signs. Then, the clinician can save the acquired patient's vital signs in the patient's electronic medical record and/or transmit the results to one or more providers.

Figure 5:
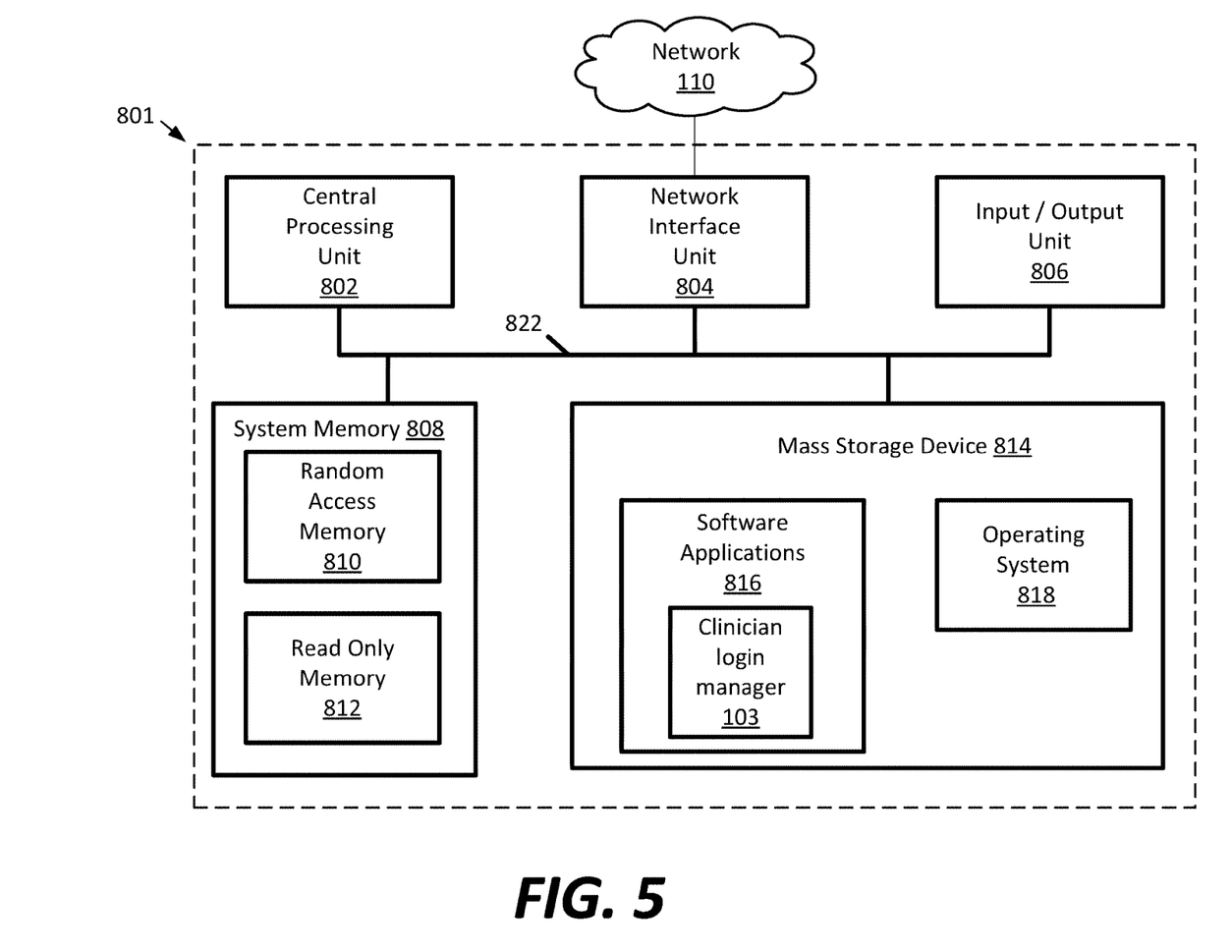
FIG. 5 shows example physical components of a computing device hosting the clinician login manager of the single sign-on system device shown in FIG. 1.

FIG. 5 shows one example of computing device 801 of the SSO system 104. As shown, example computing device 801 hosts clinician login manager 103 that is capable of executing the operations of example process 200. The SSO system 104 can include different software applications configured to manage communications with other components of environment 100 and capable of performing the operations of SSO system 104 described above.

As illustrated, the example computing device 801 includes at least one central processing unit ("CPU") 802, a system memory 808, and a system bus 822 that couples the system memory 808 to the CPU 802. The system memory 808 includes a random access memory ("RAM") 810 and a read-only memory ("ROM") 812. A basic input/output system that contains the basic routines that help to transfer information between elements within the example computing device 801, such as during startup, is stored in the ROM 812. The example computing device 801 further includes a mass storage device 814. The mass storage device 814 is able to store software applications 816 and data.

The mass storage device 814 is connected to the CPU 802 through a mass storage controller (not shown) connected to the system bus 822. The mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the SSO system 104 can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments, the example computing device 801 may operate in a networked environment using logical connections to remote network devices through the network 110, such as a wireless network, the Internet, or another type of network. The example computing device 801 may connect to the network 110 through a network interface unit 804 connected to the system bus 822. The network 110 may be a protected network, as discussed above. It should be appreciated that the network interface unit 804 may also be utilized to connect to other types of networks and remote computing systems. The example computing device 801 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing device 801 can store software instructions and data. The software instructions include an operating system 818 suitable for controlling the operation of the example computing device 801. The mass storage device 814 and/or the RAM 810 also store software applications 816, that when executed by the CPU 802, cause the example computing device 801 to provide the functionality of the example computing device 801 discussed in this document. For example, the mass storage device 814 and/or the RAM 810 can store software instructions that, when executed by the CPU 802, cause the example computing device 801 to manage clinician login at a vital signs device.

Although various embodiments are described herein, those of ordinary skill in the art will understand that many modifications may be made thereto within the scope of the present disclosure. Accordingly, it is not intended that the scope of the disclosure in any way be limited by the examples provided.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The invention claimed is:

1. A single sign-on system in a medical facility, the single sign-on system comprising:
a processing unit; and
system memory, the system memory including instructions that, when executed by the processing unit, cause the single sign-on system to:
receive, at an identity access management system, a clinician login comprising a clinician identifier and a password;
generate, at the identity management system, a grace period token for the clinician identifier, the grace period token expiring after a validation period of time;
receive, at a clinician login manager, only the clinician identifier via a first application program interface (API), the clinician identifier being received from a vital signs device, and the clinician identifier not including the password;
determine whether the clinician identifier corresponds to an entry in a user database;
transmit an authentication request to the identity access management system via a second API, the request for authentication including the clinician identifier;
receive a confirmation, via the second API, that a clinician associated with the clinician identifier is associated with an open session and within a grace period as determined by the grace period token that is not expired, wherein the open session is determined by the clinician associated with the clinician identifier having previously logged into another medical device in the medical facility using the password; and
transmit the confirmation to the vital signs device via the first API, the confirmation including an indication of successful authentication based upon only the clinician identifier.

2. The single sign-on system according to claim 1, wherein the system memory further includes instructions that, when executed by the processing unit, cause the single sign-on system to:
when the clinician identifier does not correspond to an entry in the user database, determine an alias identifier, wherein the request for authentication includes the alias identifier.

3. The single sign-on system according to claim 1, wherein the system memory further includes instructions that, when executed by the processing unit, cause the single sign-on system to:
after the vital signs device authenticates the clinician, receive vital signs data from the vital signs device.

4. The single sign-on system according to claim 3, wherein the system memory further includes instructions that, when executed by the processing unit, cause the single sign-on system to:
after the vital signs device authenticates the clinician, receive vital signs device user data;
transmit the vital signs data and the vital signs device user data to an electronic medical record (EMR) system.

5. The single sign-on system according to claim 4, wherein the vital signs device is configured to save received vital signs data only after receiving the confirmation of successful authentication; and
wherein the EMR system stores the saved vital signs data in a chart corresponding to a patient as confirmed data.

6. The single sign-on system according to claim 1, wherein the clinician associated with the clinician identifier has previously logged into an electronic medical record system or a facility workstation.

7. The single sign-on system according to claim 1, wherein the clinician identifier is at least one of: EMR user name, employee number, and network ID number.

8. The single sign-on system according to claim 1, wherein the system memory further includes instructions that, when executed by the processing unit, cause the single sign-on system to:
provide a stored security certificate to the identity access management system.

9. The single sign-on system according to claim 8, wherein the system memory further includes instructions that, when executed by the processing unit, cause the single sign-on system to:
receive, from the identity access management system, access to the user database; and
execute lookup stored procedure on the user database.

10. The single sign-on system according to claim 1, wherein the system memory further includes instructions that, when executed by the processing unit, cause the single sign-on system to:
provide a host service, the host service performing both the receive clinician identifier operation and the transmit the confirmation operation.

11. A medical device in a single sign-on system, the medical device comprising:
a processing unit; and
system memory, the system memory including instructions that, when executed by the processing unit, cause the medical device to:
receive only a clinician identifier from a clinician, the clinician identifier not including a password;
transmit the clinician identifier to a host;
receive, from the host, an authentication result, the authentication result including successful authentication or unsuccessful authentication based upon only the clinician identifier, the successful authentication determined when the clinician identifier corresponds to an entry in a user database and the clinician associated with the clinician identifier is in an open session, wherein the open session is determined by a grace period token that was generated when the clinician associated with the clinician identifier logged into another medical device in a medical facility using the password and the grace period token is not expired;
when the authentication result is successful authentication, enable clinician login without requiring the password;
acquire physiological data of a patient;
store the physiological data;
generate tagged physiological data including a clinician identifier field; and
transmit the tagged physiological data to a central monitoring station.

12. The medical device according to claim 11, wherein the system memory further includes instructions that, when executed by the processing unit, cause the medical device to:
when the authentication result is unsuccessful authentication, deny clinician login; and
deny saving the physiological data in the system memory.

13. The medical device according to claim 11, wherein the clinician identifier is acquired from at least one of the following: a radio frequency identification (RFID) badge and a bar code.

14. The medical device according to claim 11, wherein the system memory further includes instructions that, when executed by the processing unit, cause the medical device to:
receive, with the authentication result, an alias identifier, the alias identifier corresponding to the clinician identifier,
wherein generating tagged physiological data includes adding the alias ID to the clinician identifier field.

15. The medical device according to claim 11, wherein generating tagged physiological data includes adding the clinician identifier to the clinician identifier field; and
wherein physiological data include vital signs data of the patient, the vital signs data being received from a vital signs recording unit.

16. A computer-implemented method in a single-sign on system, the method comprising:
receiving only a clinician identifier that uniquely identifies a clinician from a vital signs device, the clinician identifier not including a password;
determining whether the clinician identifier corresponds to an entry in a user database;
when the clinician identifier does not correspond to an entry in the user database, determining an alias identifier, the alias identifier being an identifier associated with a clinician in the user database;
transmitting a request for authentication to an identity access management system, the request for authentication including the clinician identifier or the alias identifier;
receiving a confirmation that a clinician associated with the clinician identifier or the known identifier is associated with an open session and within a grace period, wherein the open session is determined by the clinician associated with the clinician identifier having previously logged into another medical device in a medical facility using the password and the clinician identifier being associated with a grace period token that has not expired; and
transmitting the confirmation to the vital signs device, the confirmation including an indication of successful authentication based upon only the clinician identifier.

17. The method according to claim 16, further comprising:

after transmitting the confirmation, receiving vital signs data and vital signs device user data from the vital signs device; and transmitting the vital signs data and vital signs device user data to an electronic medical record (EMR) system.

18. The method according to claim 17, further comprising:

providing a stored security certificate to the identity access management system, wherein the clinician identifier is at least one of: EMR user name, employee number, and network ID number.

19. The method according to claim 18, further comprising:

receiving a validation period, the validation period being a period of time during which a user single sign-on is enabled.

20. The method according to claim 19, further comprising:

receiving access to the user database; and executing lookup stored procedure on the user database.

* * * * *